US005746746A

United States Patent [19]

Garito et al.

[11] Patent Number: 5,746,746

[45] Date of Patent: May 5, 1998

[54] ELECTROSURGICAL ELECTRODE AND METHOD FOR SKIN RESURFACING

[76] Inventors: Jon C. Garito; Alan G. Ellman, both of 1135 Railroad Ave., Hewlett, N.Y. 11557

[21] Appl. No.: 705,600

[22] Filed: Aug. 30, 1996

[51] Int. Cl.$^6$ .......... A61B 17/39

[52] U.S. Cl. .......... 606/41; 606/45

[58] Field of Search .......... 606/32, 34, 37–42, 606/45, 49, 131–133, 167, 170–172; 607/98, 99, 112, 115, 145, 147, 149

[56] References Cited

U.S. PATENT DOCUMENTS

| | | | |
|---|---|---|---|
| 3,807,404 | 4/1974 | Weissman et al. | 606/42 |
| 4,811,733 | 3/1989 | Borsanyi et al. | 606/39 |
| 4,887,593 | 12/1989 | Wiley et al. | 606/49 |
| 5,354,296 | 10/1994 | Turkel | 606/41 |
| 5,437,665 | 8/1995 | Munro | 606/41 |
| 5,480,398 | 1/1996 | Eggers et al. | 606/39 |
| 5,505,728 | 4/1996 | Ellman et al. | 606/39 |
| 5,549,605 | 8/1996 | Hahnen | 606/49 |
| 5,569,244 | 10/1996 | Hahnen | 606/49 |

OTHER PUBLICATIONS

Laser Focus Medical Laser Buyer's Guide, 1995, A691 (2 Pages) "Skin Resurfacing Using A $CO_2$ Laser".

American Society for Dermatological Surgery, ASDS003, 1992, (2 Pages), "Chemical Peeling".

American Society for Dermatological Surgery, ASDS004, 1993, (2 Pages), "Dermabrasion Treatment".

*Primary Examiner*—Jennifer Bahr
*Assistant Examiner*—Bryan K. Yarnell

[57] ABSTRACT

An electrode for use in an electrosurgical skin resurfacing procedure. In a preferred embodiment, the electrode is uniquely configured to form an active wire segment, generally straight or bowed shape, whose width controls the width of the graft, and terminating at opposite ends in aligned coated segments, the thickness of whose coatings controls the thickness of the skin processed. The active wire is supported by structure that is completely electrically-insulated to ensure treatment only of the desired tissue while avoiding damage to surrounding tissue. Anapparatus for moving the electrode over the skin is provided in another embodiment. Finally, a method for electrosurgically resurfacing the skin is discussed.

14 Claims, 3 Drawing Sheets

32 24 10 12 22 28 30 40 26 16 28 30 34 32

ELECTROSURGICAL APPARATUS 18

ELECTROSURGICAL ELECTRODE AND METHOD FOR SKIN RESURFACING

This invention relates to an electrosurgical instrument for skin resurfacing or planing and, in particular, to an electrosurgical electrode for use in removing shallow surface layers or regions of skin in a medical or dental skin resurfacing procedure.

BACKGROUND OF THE INVENTION

Various surgical procedures are known for removing skin imperfections. One such procedure is known as dermabrasion or surgical skin planing, which is a surgical procedure in which the dermatologic surgeon removes or sands the skin with a rotary abrasive instrument. Typically, the latter comprises a high-speed hand engine with abrasive working ends, such as a wire brush or serrated wheels. This abrasive or planing action evens out the skin and a fresh layer of skin replaces the abraded skin. It can be used to improve scars or treat other skin conditions, such as tattoos, age spots, and sun damage. A problem if sufficient care is not exercised is a tendency to cut too deeply and too rapidly, since the patient's skin is frozen during the procedure and the lack of the patient's reaction to pain fails to act to limit the abrading depth.

Another surgical procedure involves use of an acid and is called chemical peeling. An acid solution is applied to the skin which causes it to blister and eventually peel off. The new regenerated skin is usually smoother. This procedure is best used to treat sun damage and fine aging lines. A problem is the requirement for bandaging and the long heeling time.

Still another surgical procedure is known as skin resurfacing with a $CO_2$ laser, which operates by vaporizing tissue to remove assorted skin imperfections. A common problem here is excessive heat conduction with resultant scarring and pigmentary changes.

SUMMARY OF THE INVENTION

An object of the invention is an improved skin planing surgical procedure using an electrosurgical instrument.

We have invented a novel electrode for use in an electrosurgical skin planing procedure. This electrosurgical procedure using our novel electrode enables physicians to offer to patients a dermatologic treatment that is efficiently performed, easily learned and thus performed at a significantly reduced cost, with less tissue damage compared to procedures done heretofore, and, most important, with precise control over the depth of skin treatment.

The procedure using our novel electrode is based on performing essentially the same kind of skin resurfacing treatments as was used heretofore but, in accordance with a feature of our invention, the structure of our novel electrosurgical electrode used to remove thin surface layers of skin prevents the treatment depth from exceeding a safe value and thus avoids the risk of digging, gouging, or excessive scarring of the skin.

In accordance with another feature of our invention, the electrode of the invention is uniquely configured to form an active, bare, electrically-conductive, thin wire segment, generally straight or slightly curved, whose width controls the width of the planing treatment, and which is terminated at opposite ends with protective electrically-insulating-coated segments each aligned with an adjacent end of the active thin wire segment. When the working active end of the activated electrode is applied to the skin region to be treated, the bare wire delivers radiofrequency energy to the contacted skin tissue causing the desired tissue planing flush with the skin surface. At the protected ends, the thickness of the electrically-insulating coating, which abuts the skin, prevents the active bare segment from digging into or gouging or scarring the tissue while limiting laterally the width of the planing action. In addition to sculpting the skin, the action also stimulates new collagen and elastin formation, tending to reduce or eliminate microwrinkles. The novel design with protected end segments will make removal of protruding lesions easier and safer, as planing flush with the surface is its major function and the electrode is virtually incapable of excavation. The active wire and its end segments are supported by structure that is completely electrically-insulated to avoid damage to surrounding tissue, and to allow the physician to use these inactive insulated parts to help position and guide the active wire segment, which is the only part capable of removing tissue, during the surgical procedure.

The electrosurgical procedure has the important advantage of being able to remove tissue with minimum surgeon pressure while at the same time coagulating the cut tissue causing minimum bleeding. It is preferred that the electrosurgical currents used be above 2 MHz, and preferably above 3 MHz. At these high frequencies, commonly referred to as radiosurgery, cutting is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
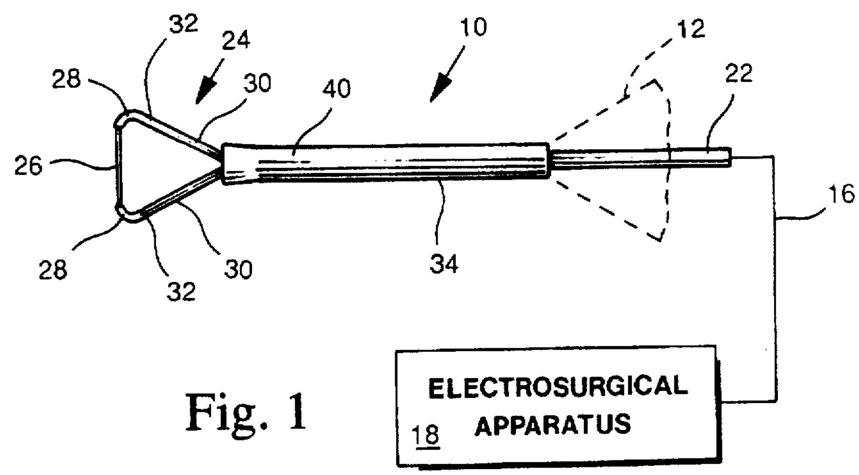
FIGS. 1 is a plan view of one form of electrosurgical instrument in accordance with the invention, shown connected to electrosurgical apparatus.

FIG. 1 illustrates a preferred form of the novel electrosurgical instrument 10 of the invention. It comprises an elongated conventional handpiece 12 (only the collet end is shown in phantom) of electrically-insulating material having a central electrically-conductive tube or conductor (not shown) extending throughout its length and connected at its end to a cable 16 which is connected in the conventional manner to conventional electrosurgical apparatus 18. As an example only, the electrosurgical apparatus can be model AAOP Surgitron FFPF available from Ellman International, Inc. of Hewlett, N.Y. The Ellman equipment is preferred due to its high operating frequency, typically above 2 MHz, preferably above 3 Mhz. This particular apparatus provides electrosurgical currents at 3.8 MHz.

At the opposite end of the handpiece 12 is mounted the electrosurgical electrode 10 which comprises an electrically-conductive straight axial brass rod 22 running lengthwise through it and mounted at its end nearest the handpiece 12 in the handpiece collet and thus electrically connected to the electrically-conductive cable 16. The distal end of the electrode comprises an electrically-conductive, generally triangular member 24 whose ends (not shown) are electrically connected to the brass rod 22. The segments of the triangle are preferably constituted of tungsten wire. Also connected to the electrosurgical apparatus 18 is the usual indifferent plate (not shown) which during use is in contact with a patient's body. When the electrosurgical apparatus 18 is energized, high frequency electrosurgical currents are generated which are coupled by way of the cable 16 and electrically-conductive rod 22 to the tungsten wire in the triangular shape 24. The physician, in the usual way, holds the handpiece 12 while applying the active working end of the electrode to the desired area of the patient to be treated.

In accordance with a feature of the invention, the wire member 24 comprises an active bare wire segment 26 whose end segments 28 and side segments 30 are coated with a thin electrically-insulating coating 32. The shank 40 is also coated with an electrically-insulating coating 34. The active thin wire 26 has, for example, a thickness of about 0.007 inches in diameter of tungsten, preferably between about 0.004 and 0.010 inches, and extends generally transverse to the longitudinal axis of the straight shaft 22 of the electrode. The coating 34 for the straight shaft part of the electrode may be one of many suitable electrically-insulating rubber or plastic materials. The coating 32 on the triangular member 24 comprises a thinner coating of an electrically-insulating material, which may be one of many suitable thin electrically-insulating plastics, baked Teflon being one example. Thus, the entire length of the electrode 10 from the bare active wire end 26 to the opposite bare end 22 which is mounted in the handpiece 12 is electrically insulated from the patient. The handpiece 12, too, is completely electrically-insulated. The end segments 28 curve around the wire and are aligned with the transverse active wire 26. The thin coating 32 on the end segments 28 preferably has a thickness in the range of about 0.002–0.008 inches, preferably about 0.004 inches.

Figure 2:
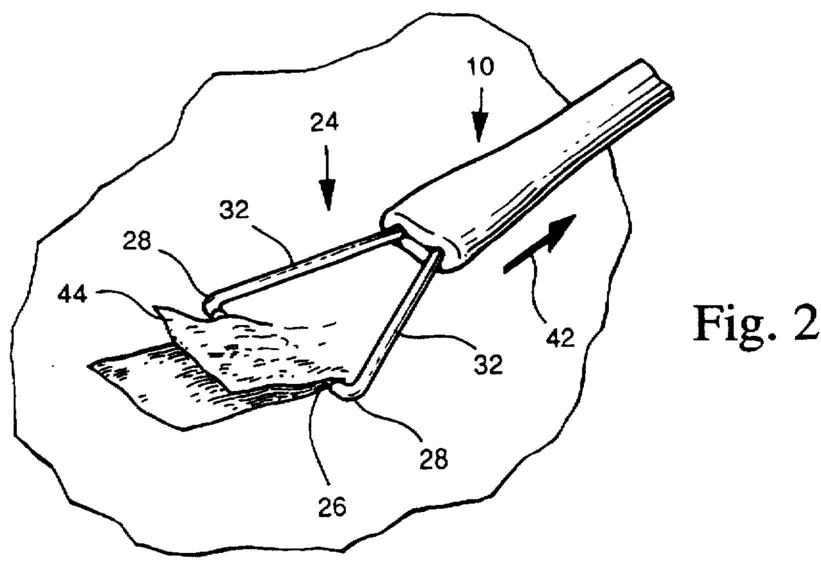
FIGS. 2 and 3 are perspective views showing how the electrosurgical instrument according to the invention can be used in a skin planing operation.
Figure 3:
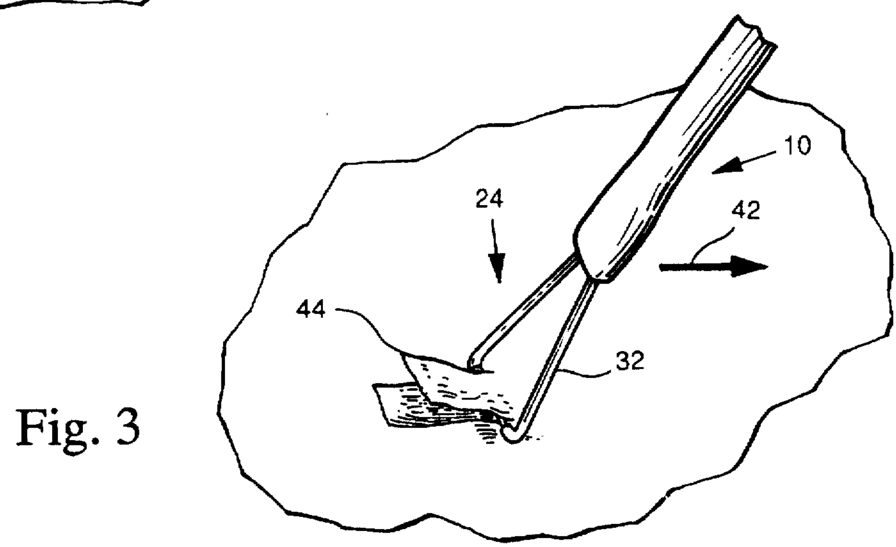

In use, as illustrated for two electrode positions in FIGS. 2 and 3, the bottom segment comprising the active bare segment 26 and the coated end segments 28 are pressed against the skin of the patient being treated. When the apparatus is activated and the eltrode moved across the skin of the patient, the bare active end 26 barely penetrates into the tissue to a depth controlled by the thickness of the coatings 32 at the segment ends 28, of the order of about several thousands of an inch. This is sufficient to remove a thin surface layer of skin 44 whose width is that of the bare wire 26. The active wire 26 cuts cleanly and easily with little pressure required through the tissue. The end segments 28 prevent the straight or gently curved exposed wire 26 from drifting below the surface while the bare wire 26 delivers a dose of electrosurgical currents to gently plane the skin surface and shallow dermis.

The width of the bare wire 26, in the transverse direction, is preferably in the range of about 0.2–0.5 inches, preferably about 0.3 inches. For different skin treatments, is is desirable to provide a family of electrodes with different active wire diameters and different active wire widths.

The shape of the active wire end 28, while preferably round, is not restricted to that shape. It can also have a tapered shape such that the leading edge of the wire is narrower than the trailing edge. The insulating coatings 32 and 34 are essential to prevent accidental burning or other tissue damage by the sides of the electrode as the instrument is manipulated over the skin of the patient.

Figure 4:
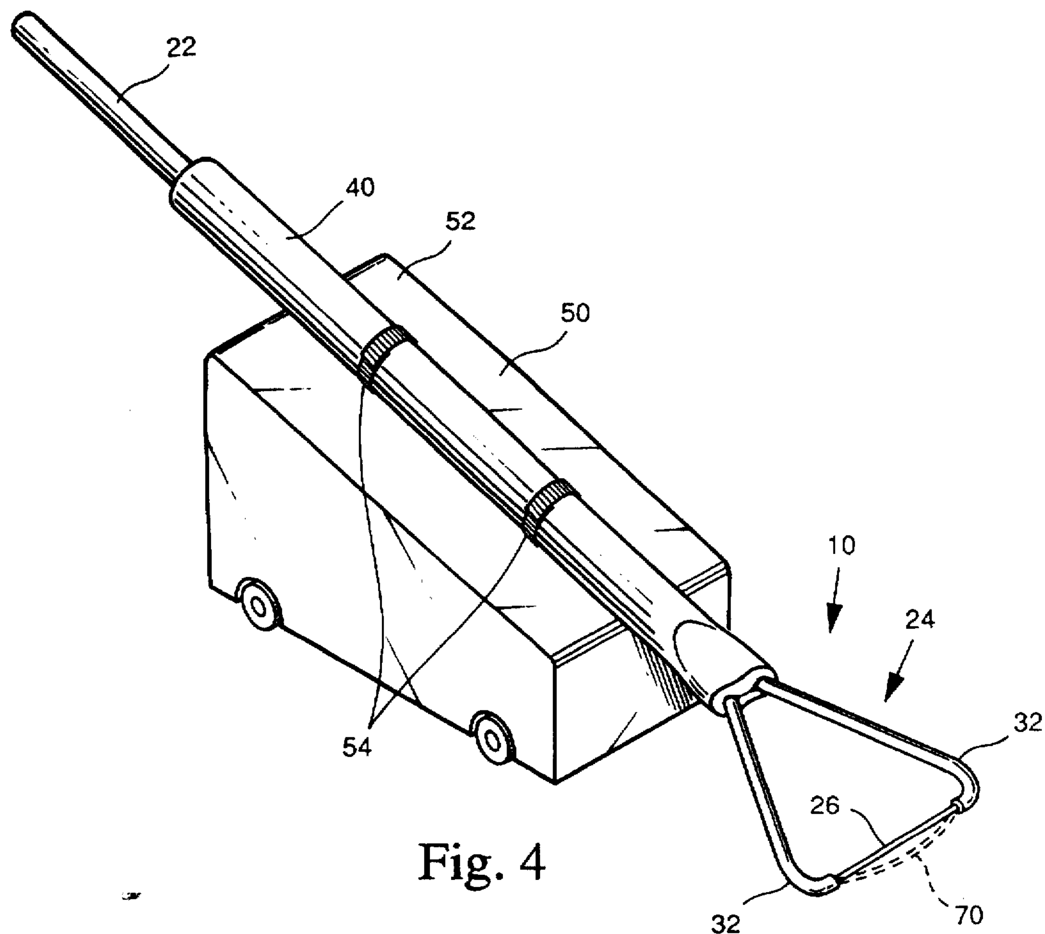
FIGS. 4–6 are perspective views of variants of an electrosurgical instrument according to the invention.
Figure 5:
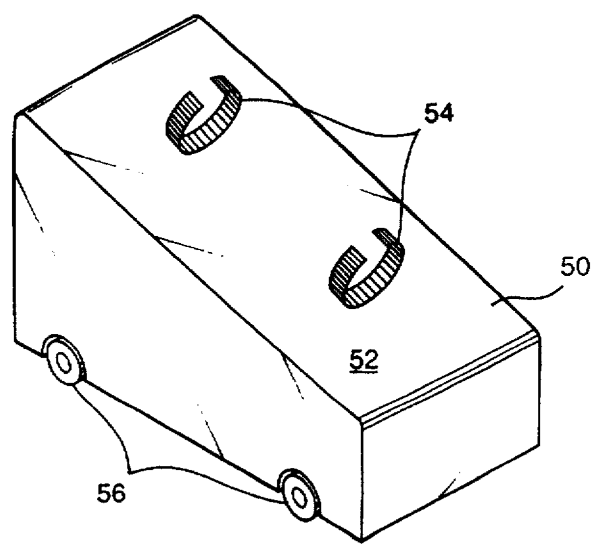
Figure 6:
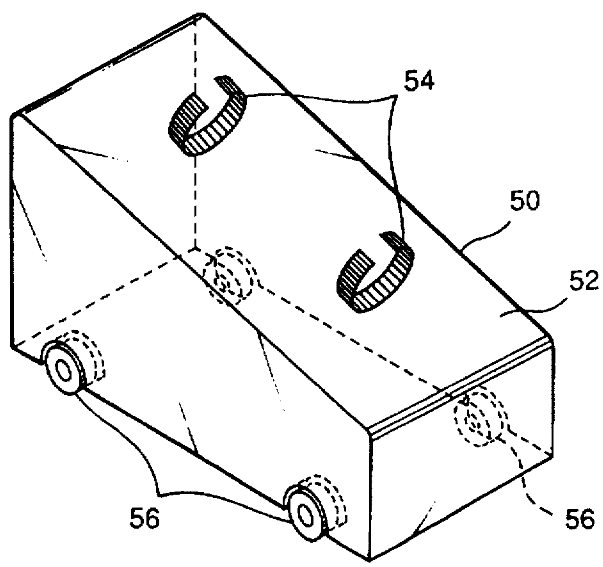

FIGS. 4–6 and 7 show modified electrode configurations. In the embodiment of FIGS. 4–6, in order to make it easier to move the electrode 10 over the skin of a patient, the electrode 10 is removably mounted on a small movable guide member such as, for example, a small cart 50 with a slanted top 52 provided with two clamps 54 for the electrode shank 40. The cart is provided at the bottom with four small wheels 56 mounted for free rotation on axles secured to the sides of the cart 50. The electrode as shown in FIG. 4 can be mounted on the clamps 54 so the working wire end 26 projects forward of the cart in a position to engage the skin surface. The forward position of the electrode 10 can be adjusted within the clamps 54. This allows the pressure on the skin to be adjusted to the physician's satisfaction. FIG. 5 shows the cart 50 without the electrode 10, and FIG. 6 shows some interior details of the cart. The presence of the wheeled cart supporting the electrode 10 reduces friction and makes for a smoother movement over the patient's skin without fear of overcutting. All parts of the cart are preferably electrically-insulating to avoid undesired tissue damage.

Figure 7:
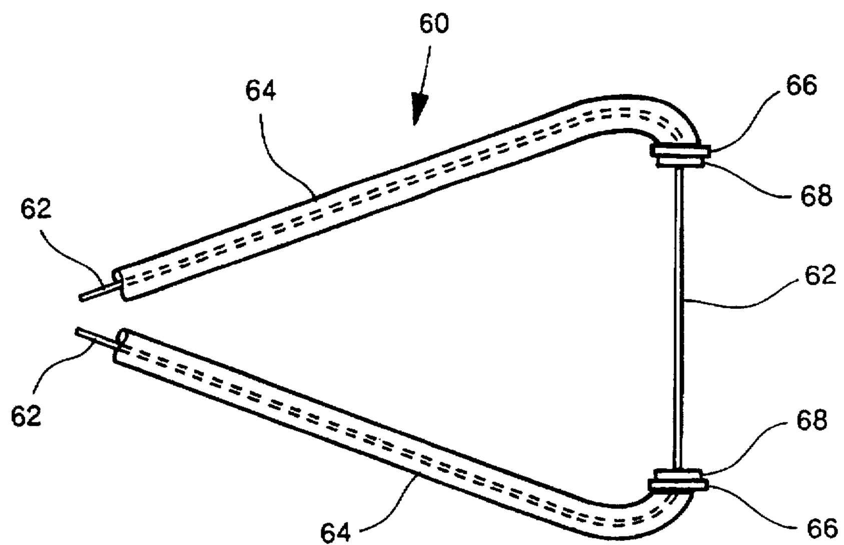
FIG. 7 is a plan view of a further variant of an electrosurgical instrument according to the invention.

In the modification shown in FIG. 7, which illustrates only the working end of an electrode 60, the remaining back end being similar to the FIG. 1 embodiment, another wheeled construction is illustrated. In this case, the wire 62 in front is bared, and is coated with a thin insulator 64 as before. In this case, however, the insulator sections adjacent the bare wire are separated into a thin annular sleeve 66 which is not adherent to the wire and is thus free to rotate, and an adjacent slightly thinner annular sleeve 68 which is adherent to the wire 62 and remains fixed. The rotatable members 66 serve as wheels which allow the physician to move the electrode 60 more smoothly over the patient's skin. In this case, the not-shown end of the electrode is mounted in and supported by a handpiece in the same manner as in FIG. 1. The embodiment of FIG. 7 has the advantage over the embodiment of FIG. 4 in that the physician can adjust the tilt of the electrode as illustrated in FIGS. 2 and 3.

Occasionally, it becomes desirable to work on an area of the patient where the skin is not planar but somewhat concave. In such a case, it is desirable to use an active wire shape that is complementary to that of the skin being treated. This is easily achieved, as is illustrated in FIG. 4 by dashed lines, by a slight bowing 70 of the active wire bight portion, with the remaining parts of the electrode remaining the same. A 0.007 inches wire of tungsten is sufficiently stiff to hold the bowed shape imparted to it during manufacture. A typical bowing radius is about 0.3–0.6, preferably about 0.4, inches. Hence, with relative ease, the family of electrodes can be enlarged to include several sizes of electrodes with bowed active wire portions for use with skin areas that are curved.

With the Ellman equipment, the fully rectified or cut/coag current is used at a power setting of about 3–4 with the active bare wire electrode 26. There is very little trauma and the sore area felt by the patient at the treated site is easily handled by analgesia and anti-inflammatory drugs.

It will also be understood that the electrode of the invention is not limited to its use for a skin planing or surface procedure. To those skilled in this art, there will certainly be other uses for this novel electrode that provides a straight or bowed active wire segment with adjacent electrode end segments coated with insulating material for accurately guiding and controlling the position of the active wire during a tissue resurfacing electrosurgical procedure.

For completeness' sake, it is noted that a copending patent application, Ser. No. 08/593010, filed Jan. 29, 1996, and now U.S. Pat. No. 5,683,387, describes for skin grafting an electrosurgical electrode that is uniquely configured to form a U-support terminating in an active wire, generally U-shaped, whose width controls the width of the graft, and the length of whose arms, transverse to the active wire, controls the thickness of the graft. The active wire is supported by structure that is completely electrically-insulated to ensure excision only of the desired tissue while avoiding damage to surrounding tissue. The tissue incising is effected with the bare active wire at a depth stopped by a shoulder between the bare wire arms and the adjacent portions of the electrode support. This structure determines skin-removal depth by the length of the bare wire portion extending generally parallel to the shaft axis from the shoulder separating the coated part of the arms from the active bare wire. In the present invention, the depth of skin planing is determined, in the preferred embodiment, by the thickness of the insulating coating, and the active bare wire is an extension of, aligned with, and located between the coated end segments.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for tissue planing, comprising:

(a) an electrically-conductive shaft member having a longitudinal direction and a first end for mounting to a handpiece and a second end, (b) said second end comprising an active, electrically-conductive, exposed wire portion having a generally straight shape extending generally transverse to the shaft member and terminated at opposite ends by end segments generally aligned with and lying in the same plane as that of the active wire portion, the end segments terminating said exposed wire portion being provided with a coating of a thickness such that, when the active wire portion is applied to tissue, the coating prevents the exposed active wire portion from digging into, gouging or scarring the tissue, (c) said active wire portion being exposed electrically for applying electrosurgical currents to said tissue when said shaft member is connected to a source of electrosurgical currents, (d) the coating on the end segments terminating said exposed wire portion being electrically-insulating to prevent contact and passage of electrosurgical currents to areas adjacent to or surrounding the tissue to be treated and controlling the depth of tissue treated.

2. An electrosurgical electrode as claimed in claim 1, wherein the active wire portion has a length in its tranverse direction of about 0.2–0.5 inches.

3. An electrosurgical electrode as claimed in claim 1, wherein the active wire portion is constituted of a thin wire having a diameter of about 0.004–0.010 inches.

4. An electrosurgical electrode as claimed in claim 1, wherein the electrical insulation of the end segments is constituted by a coating having a thickness in the range of about 0.002–0.008 inches.

5. An electrosurgical electrode as claimed in claim 1, wherein the active wire portion is supported by a generally triangular support.

6. An electrosurgical electrode for tissue planing, comprising:

(a) an electrically-conductive shaft member having a longitudinal direction and a first end for mounting to a handpiece and a second end, (b) said second end comprising an active, electrically-conductive, wire portion having a generally straight or bowed shape extending generally transverse to the shaft member and terminated at opposite ends by end segments generally aligned with the active wire portion, (c) said active wire portion being exposed electrically for applying electrosurgical currents to said tissue when said shaft member is connected to a source of electrosurgical currents, (d) the end segments adjacent said exposed wire portion being electrically-insulating to prevent contact and passage of electrosurgical currents to areas adjacent to or surrounding the tissue to be treated and controlling the depth of tissue treated, (e) means for rolling the exposed wire portion of the electrode over the tissue to be planed.

7. An electrosurgical electrode as claimed in claim 6, wherein the means for rolling comprises a movable guide member for removably supporting the active wire portion.

8. An electrosurgical electrode as claimed in claim 6, wherein the means for rolling comprises rotatable sleeves adjacent each of the end segments.

9. In combination:

i) electrosurgical apparatus capable of supplying high frequency currents, ii) an electrosurgical electrode having an electrically-conductive shaft;

iii) a handpiece having means at one end for connection to the electrosurgical apparatus and having at its opposite end means for mounting to the electrically-conductive shaft of the electrosurgical electrode and for supplying the high frequency currents to said electrode;

said electrode comprising:

(a) a first end for mounting to the handpiece and a second end and having a longitudinal direction between the first and second ends, (b) said second end comprising an active, electrically-conductive, wire portion having a generally straight or bowed shape extending generally transverse to the shaft member and terminated at opposite ends by end segments generally aligned with the active wire portion, (c) said active wire portion being exposed electrically for applying electrosurgical currents to said tissue when said shaft member is connected to a source of electrosurgical currents, (d) the end segments terminating said exposed wire portion being provided with an electrically-insulating coating to prevent contact and passage of electrosurgical currents to areas adjacent to or surrounding the tissue to be treated, the thickness of said electrically-insulating coating being selected to control the depth of tissue treated.

10. The combination of claim 9, wherein the high frequency currents are at a frequency exceeding 2 MHz.

11. In combination:

i) electrosurgical apparatus capable of supplying high frequency currents, ii) an electrosurgical electrode having an electrically-conductive shaft, iii) a handpiece having means at one end for connection to the electrosurgical apparatus and having at its opposite end means for mounting to the electrically-conductive shaft of the electrosurgical electrode and for supplying the high frequency currents to said electrode, said electrode comprising:

(a) a first end for mounting to the handpiece and a second end and having a longitudinal direction between the first and second ends, (b) said second end comprising an active, electrically-conductive, wire portion having a generally straight or bowed shape extending generally transverse to the shaft member and terminated at opposite ends by end segments generally aligned with the active wire portion, (c) said active wire portion being exposed electrically for applying electrosurgical currents to said tissue when said shaft member is connected to a source of electrosurgical currents, (d) the end segments terminating said exposed wire portion being electrically-insulating to prevent contact and passage of electrosurgical currents to areas adjacent to or surrounding the tissue to be treated and controlling the depth of tissue treated, iv) further comprising means for supporting the active wire portion for rolling contact with the tissue.

12. A skin planing surgical procedure for a patient, comprising the steps:

(a) providing electrosurgical apparatus connected to a handpiece holding an electrosurgical electrode, said electrosurgical electrode comprising:

(a) an electrically-conductive shaft member having a longitudinal direction and a first end for mounting to a handpiece and a second end, (b) said second end comprising an active, electrically-conductive, wire portion having a generally straight or bowed shape extending generally transverse to the shaft member and terminated at opposite ends by end segments generally aligned with the active wire portion, (c) said active wire portion being exposed electrically for applying electrosurgical currents to said tissue when said shaft member is connected to a source of electrosurgical currents, (d) the end segments adjacent said exposed wire portion being electrically-insulating to prevent contact and passage of electrosurgical currents to areas adjacent to or surrounding the tissue to be treated and controlling the depth of tissue treated, (b) applying the active wire portion of the electrode to the skin of a patient and activating the electrosurgical apparatus, (c) moving the active wire portion of the electrode over the skin of the patient to be planed.

13. An electrosurgical electrode for tissue planing, comprising:

(a) an electrically-conductive shaft member having a longitudinal direction and a first end for mounting to a handpiece and a second end, (b) said second end comprising an active, electrically-conductive, wire portion having a slightly bowed shape extending generally transverse to the shaft member and terminated at opposite ends by end segments generally aligned with and lying in the same plane as that of the active wire portion, the end segments terminating said exposed wire portion being provided with a coating of a thickness such that, when the active wire portion is applied to tissue, the coating prevents the exposed active wire portion from digging into, gouging or scarring the tissue, (c) said active wire portion being exposed electrically for applying electrosurgical currents to said tissue when said shaft member is connected to a source of electrosurgical currents, (d) the coating on the end segments terminating said exposed wire portion being electrically-insulating to prevent contact and passage of electrosurgical currents to areas adjacent to or surrounding the tissue to be treated and controlling the depth of tissue treated.

14. An electrosurgical electrode as claimed in claim 13, wherein the active wire portion is slightly concave viewed from the shaft member.

* * * * *